United States Patent
Da Silva et al.

(10) Patent No.: US 10,024,756 B2
(45) Date of Patent: Jul. 17, 2018

(54) METHOD AND SYSTEM FOR STRUCTURAL HEALTH MONITORING WITH FREQUENCY SYNCHRONIZATION

(71) Applicants: Embraer S.A., São José dos Campos (BR); PUC-RIO, Rio de Janeiro (BR)

(72) Inventors: Paulo Anchieta Da Silva, Sao Jose dos Campos (BR); Fernando Dotta, Sao Jose dos Campos (BR); Laudier Jacques De Moraes Da Costa, Sao Jose dos Campos (BR); Arhur Martins Barbosa Braga, Rio de Janeiro (BR); Luiz Carlos Guedes Valente, Rio de Janeiro (BR); Daniel Ramos Louzada, Rio de Janeiro (BR); Leonardo Salvini, Rio de Janeiro (BR); Paula Medeiros Proença De Gouvêa, Rio de Janeiro (BR)

(73) Assignees: Embraer S.A., São José dos Campos (BR); PUC-RIO (Pontificia Universidade Católica do Rio de Janeiro), Rio de Janeiro (BR)

( * ) Notice: Subject to any disclaimer, the term of this patent is extended or adjusted under 35 U.S.C. 154(b) by 471 days.

(21) Appl. No.: 14/526,226

(22) Filed: Oct. 28, 2014

(65) Prior Publication Data

US 2016/0116366 A1   Apr. 28, 2016

(51) Int. Cl.
*G01L 1/16* (2006.01)
*G01M 7/00* (2006.01)
*G01L 1/24* (2006.01)
*G01M 5/00* (2006.01)
*G01N 29/11* (2006.01)
*G01N 29/34* (2006.01)
*G01N 29/44* (2006.01)

(52) U.S. Cl.
CPC ............... *G01M 7/00* (2013.01); *G01L 1/167* (2013.01); *G01L 1/246* (2013.01); *G01M 5/0033* (2013.01); *G01M 5/0041* (2013.01); *G01M 5/0066* (2013.01); *G01N 29/11* (2013.01); *G01N 29/345* (2013.01); *G01N 29/348* (2013.01); *G01N 29/4436* (2013.01); *G01N 2291/012* (2013.01); *G01N 2291/0258* (2013.01); *G01N 2291/103* (2013.01)

(58) Field of Classification Search
CPC ........................................................ G01L 1/167
See application file for complete search history.

(56) References Cited

U.S. PATENT DOCUMENTS 5,184,516 A   2/1993 Blazic et al.
5,814,729 A   9/1998 Wu et al.
(Continued)

OTHER PUBLICATIONS

Guo et al., "Fiber Optic Sensors for Structural Health Monitoring of Air Platforms", Sensors, 2011, 11, 3687-3705, Mar. 25, 2011.*
(Continued)

*Primary Examiner* — Jennifer Simmons
(74) *Attorney, Agent, or Firm* — Nixon & Vanderhye P.C.

(57) ABSTRACT

Structural health monitoring ("SHM") methods, apparatus and techniques involve building deformation fields maps (amplitude and phase related to excitation) on the surface of the structural component under monitoring based on a network of strain measurements by fiber Bragg grating sensors.

12 Claims, 3 Drawing Sheets

(56) References Cited

U.S. PATENT DOCUMENTS

| | | | |
|---|---|---|---|
| 6,006,163 A * | 12/1999 | Lichtenwalner | G01H 5/00 |
| | | | 702/34 |
| 6,233,085 B1 * | 5/2001 | Johnson | G02F 1/0121 |
| | | | 356/5.09 |
| 6,370,964 B1 | 4/2002 | Chang et al. | |
| 6,399,939 B1 | 6/2002 | Sundaresan et al. | |
| 7,017,421 B2 | 3/2006 | Kehlenbach | |
| 7,281,428 B2 | 10/2007 | Kim | |
| 7,426,447 B2 | 9/2008 | Pado | |
| 7,536,911 B2 | 5/2009 | Kim | |
| 8,020,444 B2 | 9/2011 | Yu et al. | |
| 8,371,170 B2 | 2/2013 | Masuda | |
| 2003/0167141 A1 | 9/2003 | Staszewski | |
| 2011/0035088 A1 * | 2/2011 | White | G01N 29/04 |
| | | | 701/31.4 |
| 2012/0203474 A1 | 8/2012 | Kawiecki et al. | |

OTHER PUBLICATIONS

Takahashi et al., "High Precision Operation of Fiber Bragg Grating Sensor with Intensity-Modulated Light Source", Experimental Analysis of Nano and Engineering Materials and Structures. Springer Netherlands, 2007. 169-170.*

Song et al., "Multiplexing control of a multichannel piezoelectric deformable mirror", Proceedings of SPIE—The International Society for Optical Engineering, Dec. 2005.*

* cited by examiner

METHOD AND SYSTEM FOR STRUCTURAL HEALTH MONITORING WITH FREQUENCY SYNCHRONIZATION

CROSS-REFERENCE TO RELATED APPLICATIONS

None.

STATEMENT REGARDING FEDERALLY SPONSORED RESEARCH OR DEVELOPMENT

None.

FIELD

The technology herein relates to the field of structural health monitoring ("SHM"), and more specifically, to methods and systems for structural health monitoring of composite, metal or other structures, based on the measurement of the deformation field on the surface under test and comparison with an initial or otherwise known signature(s) of the (non-defective) structure through a scan of a frequency range and evaluation of the amplitude (or RMS value or peak-to-peak value) of different sensors near resonance(s). Still more particularly, methods, apparatus and techniques provided by the present example non-limiting embodiment comprise or involve building deformation fields maps (amplitude and phase related to excitation) on the surface of the structural component under monitoring based on a network of strain measurements by fiber Bragg grating sensors.

BACKGROUND

As all structures in service may require appropriate inspection and maintenance, they should be monitored for their integrity and health condition to extend their life or to prevent catastrophic failure. Numerous techniques have been employed to identify fault or damage of structures. Such techniques include conventional visual inspection and non-destructive automated techniques including ultrasonic and eddy current scanning, acoustic emission and X-ray inspection. Such conventional techniques often require at least temporary removal of structures from service for inspection. Although still widely used for inspection of isolated locations, they are often time-consuming and expensive and may not be suitable on their own for inspecting equipment such as aircraft while the equipment is in service.

Such approaches have other drawbacks and may not provide effective on-line methods to implement a reliable sensory network system and/or accurate monitoring methods that can diagnose, classify and/or forecast structural condition with minimum intervention of human operators.

With the advance of sensor technologies, new diagnostic techniques for in-situ structural integrity monitoring have made significant progress. Typically, these new techniques utilize sensory systems of appropriate sensors and actuators built into host structures.

Some SHM systems use "passive" strain tracking or acoustic emission monitoring techniques. However, to effectively detect damage in many applications, both passive strain tracking and passive acoustic emission monitoring techniques may require continuous monitoring. Accordingly, if a power failure or power shut-down occurs, the SHM system may be disabled—which can be a disadvantage. Moreover, both passive strain tracking and passive acoustic emission monitoring may not be as sensitive as desired, and therefore may be less accurate and/or reliable. The accuracy and reliability of acoustic emission monitoring techniques may also be compromised by the generally noisy environment of a vehicle or other environment. Another possible disadvantage of acoustic emission monitoring is that a large amount of data storage may be necessary. To quantify and localize the damage, the strain tracking technique may require a finite element strain distribution model with which to compare the measured strain distribution across the structure, possibly increasing development cost.

Other SHM systems may be considered "active" systems because they use transducers to actively excite and sense vibrational characteristics of the structure. The vibrational characteristics can be compared with known or baseline (and thus predetermined) vibrational characteristics of a normal undamaged structure; and the difference(s) is used to determine the health of the structure. Specifically, in some SHM systems, the vibrational characteristics can be defined by computing the transfer function between each actuator and sensor. The transfer functions can then be compared to a baseline reference representing a normal "healthy" state of the structure. The baseline may be generated by collecting several sets of actuator/sensor data when the structure is healthy, and computing statistical values such as the mean and standard deviation of the data sets. However, temperature variations of the structure may sometimes cause these active SHM systems to erroneously detect damage. Specifically, temperature variations in the structure may cause variations in the measured vibrational characteristics that carry over into the transfer functions computed therefrom.

Known techniques often follow one of two approaches: signal excitation and processing on the one hand, and on the other hand, worked signal and results.

For example, methods are known that detect changes of damping characteristics of vibrational waves in a laminated composite structure to locate delaminated regions in the structure. Piezoceramic devices can be applied as actuators to generate the vibrational waves, and fiber optic cables with different grating locations can be used as sensors to catch or sense the propagating wave signals. A possible drawback of this type of system is that it cannot accommodate a large number of actuator arrays and, as a consequence, each of actuators and sensors must be placed individually. Since the damage detection is based on changes of vibrational waves traveling along line-of-sight paths between the actuators and sensors, such a method may fail to detect the damage located out of the paths and/or around the boundary of the structure.

Another known approach for damage detection uses a self-contained conformal circuit for structural health monitoring and assessment. Such a conformal circuit may for example consist of a series of stacked layers and traces of strain sensors, where each sensor measures strain changes at its corresponding location to identify defects of a conformal structure. The conformal circuit may for example comprise a passive system, i.e., it does not have any actuator for generating signals. Another example passive sensory network system may use a piezoceramic-fiber sensory system having planer fibers embedded in a composite structure.

A possible drawback of these and other passive methods is that they cannot monitor internal delamination and damage between the sensors. Moreover, these methods can typically detect the conditions of their host structures only in the local areas where the self-contained circuit and the piezoceramic-fiber are affixed.

Another interesting method for detecting damages in a structure uses a sensory network layer, called Stanford Multi-Actuator-Receiver Transduction (SMART) Layer. The SMART Layer® includes piezoceramic sensors/actuators equidistantly placed and cured with flexible dielectric films sandwiching the piezoceramic sensors/actuators ("piezoceramics"). The actuators generate acoustic waves and sensors receive/transform the acoustic waves into electric signals. To connect the piezoceramics to an electronic box, metallic clad wires are etched using conventional flexible circuitry and laminated between the substrates. As a consequence, a considerable amount of the flexible substrate area may be needed to cover the clad wire regions. In addition, the SMART Layer® may need to be cured with its host structure made of laminated composite layers. Due to the internal stress caused by a high temperature cycle during the curing process, the piezoceramics in the SMART Layer® can be micro-fractured. Also, the substrate of the SMART Layer® can sometimes be easily separated from the host structure. Moreover, it can be very difficult to insert or attach the SMART Layer® to its host structure having a curved section and, as a consequence, a compressive load applied to the curved section can sometimes easily fold the clad wires. Fractured piezoceramics and the folded wires may be susceptible to electromagnetic interference noise and provide misleading electrical signals. In harsh environments, such as thermal stress, field shock and vibration, the SMART Layer® may not necessarily be a robust and unreliable tool for monitoring structural health. Furthermore, the replacement of damaged and/or defective actuators/sensors may sometimes be costly as the host structure may need to be dismantled.

Another known actuator and sensor system is known for use with composite structures, especially carbon-fiber reinforced plastic structures with piezo-ceramic actuators, particularly for active vibration dampening and/or shape control purposes, as well as fiber Bragg grating sensors, particularly in the form of strain measurement sensors. The piezoceramic actuators are designed as piezo fiber modules and the fiber Bragg grating sensors are at least partially embedded in the piezo fiber modules. Yet another known interrogation systems for monitoring structural health conditions includes at least one wave generator for generating a wave signal and optical fiber sensors applied to a structure. The interrogation system also includes at least one electronic module for generating an input sensor signal and sending the input sensor signal to the optical fiber sensors. Each optical fiber sensor impresses the wave signal onto the input sensor signal to generate an output sensor signal that is frequency shifted from the input sensor signal. The electronic module generates an information signal in response to the output sensor signal. The interrogation system also includes a signal processing unit and a relay switches array module. Each relay switch relays the information signal to the signal processing unit and the signal processing unit generates a digital sensor signal that is subsequently sent to a computer.

Yet another known method for monitoring damage to a structure having an actuator and a sensor includes exciting the actuator across a predetermined frequency range to excite the structure, measuring a vibrational characteristic of the structure across the predetermined frequency range in response to the excitation of the actuator using the sensor, calculating a transfer function for the actuator and the sensor using the measured vibrational characteristic, determining a change in the vibrational characteristic across the predetermined frequency range using the transfer function, and analyzing the determined change in the vibrational characteristic across the predetermined frequency range to facilitate determining whether the structure is damaged.

Other known devices for monitoring structural health conditions of host structures include at least one optical fiber sensor and an electronic module. The optical fiber sensor includes a rolled optical fiber cable operative to generate a frequency shift of a light signal passing through the optical fiber and a coating layer applied to the rolled optical cable. The frequency shift is commensurate with vibration of the host structure. The electronic module sends an input light signal to the optical fiber sensor, receives a sensor signal from the optical fiber sensor, and processes the sensor signal.

Yet another known method for optimizing transducer performance in an array of transducers in a structural health monitoring system includes specifying a plurality of paths between pairs of the transducers on a monitored structure and evaluating the quality of signal transmissions along the paths so as to optimize the gain and frequency operating condition of the transducers.

In yet another known method for diagnosis of a structure, at least one electromechanical transducer is fixed to a structure as an object of diagnosis and is driven with an alternating voltage of a constant amplitude, and a current flowing through the at least one electromechanical transducer is measured. Next, high frequency components around a driving frequency of the electromechanical transducer are separated from a signal of the current. Next, modulation information due to a damage is extracted from amplitude and/or phase demodulation of the high frequency components. Then a damage index is evaluated based on the modulation information. Thus, structural health can be diagnosed with use of at least one electromechanical transducer, without baseline data, in one measurement.

Yet another known method relates to testing structures or bodies to determine if they contain defects such as cracks or delamination. Such a method for testing a body comprises the steps of comparing first data, representing an excitation signal launched into the body to produce a guided wave within the body, with second data, derived from the body while bearing the guided wave, to identify a phase difference between the first and second data; and determining a measure of the structural integrity of the body using the phase difference. It is alleged that by basing the assessment of the structural body on defect induced phase modulation, more accurate testing can be performed.

Another known structural health monitoring system, for example a system used in the non-destructive evaluation of an aircraft structure provides a method and apparatus for evaluating one or more anomalies within a structure using a structural health monitoring system that includes at least three transducers arranged in operative contact with the structure such that no two transducers are aligned to be parallel. A transducer excites an elastic wave that propagates through the structure, and reflections from any anomalies within the structure are collected by the three transducers. These collected signals are analyzed to identify an anomaly within the structure. Time of flight techniques are used to determine the location of the anomaly.

The working of the signal envisaged in non-limiting example embodiments herein is unique at least because the signal working involves matching phase and amplitude, while many other known techniques are directed for the working of phase alone or amplitude alone. By matching phase and amplitude, many advantages are obtained, such as much finer resolution for the strain measurement with the Bragg grating sensors. These features are summarized in Tables 1 and 2 below.

TABLE 1

SIGNAL EXCITATION AND PROCESSING

| | SIGNAL EXCITATION | | | SIGNAL PROCESSING | | |
|---|---|---|---|---|---|---|
| | Mechanical Vibration | Electricity | Acoustic Emissions | Time of Flight | Statistical Analyses | Neural Networks |
| Technique 1 | | | x | | x | |
| Technique 2 | | | x | | x | |
| Technique 3 | x | | | | x | |
| Technique 4 | | | x | x | x | |
| Technique 5 | | | x | | x | |
| Technique 6 | | | x | | x | |
| Technique 7 | | x | | | x | |
| Technique 8 | | | x | | x | |
| Technique 9 | | | x | | x | |
| Example Non-Limiting Embodiments Herein | x | | | | x | x |

TABLE 2

WORKING OF SIGNAL AND RESULTS

| | WORKING OF SIGNAL | | | | RESULTS | | |
|---|---|---|---|---|---|---|---|
| | Freq. | Amplitude | Phase | Matched Phase and Amplitude | Detection | Location | Severity |
| Technique 1 | | x | | | x | | |
| Technique 2 | x | x | x | | x | | |
| Technique 3 | | | | | x | x | x |
| Technique 4 | x | | | | x | x | x |
| Technique 5 | x | | | | x | | |
| Technique 6 | | x | | | x | | |
| Technique 7 | | x | x | | x | | |
| Technique 8 | | | x | | x | | |
| Technique 9 | | x | | | x | | |
| Example Non-Limiting Embodiments Herein | | | | x | x | x | x |

SUMMARY

Methods, apparatus and techniques provided by the present example non-limiting embodiments comprise or involve building deformation fields maps (amplitude and phase related to excitation) on the surface of the structural component under monitoring based on a network of strain measurements by fiber Bragg grating sensors.

The mapped deformation fields are obtained from the excitation of the structural component by piezoelectric actuators attached to and/or embedded into the structural component.

Several frequencies can be used for excitation, one frequency at a time, yielding further deformation fields which add to the one already existing on the structure resulting from primary and secondary loads on the structure.

The fact that the deformations imparted by the piezoelectric elements attached to the element surface are very small secures the linearity of the response and allows the application of the superimposition principle.

Thus, the signals captured by the optical sensors may be filtered so as to measure only the deformations of the same frequency used for the excitation, that is, just the contribution to the field brought by the piezoelectric actuators.

The so-obtained deformation maps are compared with a previously obtained standard or baseline map which is the structural component without any deformation or with a defect of known dimensions and positions.

An artificial intelligence algorithm can be employed in some non-limiting embodiments so that based on the initial standard or baseline, it is possible to detect, locate and quantify new faults or failures or alternatively monitor the growth of any previously detected fault or damage.

Thus, in one non-limiting aspect, a method is provided for monitoring damage to a structure having at least an actuator and at least a sensor. The method includes exciting in-phase or out-of-phase the at least one actuator or a group of actuators, or all the actuators using CW (continuous wave) across a predetermined frequency range to excite the structure, so as to generate a dynamic deformation field, with senoidal (sinusoidal) timed variation at the same frequency of the potential difference imposed on the piezoelectric elements. The deformation field superimposes on the already existing deformation field on the structural component caused by primary and secondary loads which act on the structural component, including those related to temperature. In example non-limiting embodiments, the choice of the frequency of actuation is made to be different from the frequency ranges associated with the primary and secondary loads as well as to temperature variations in the structural component. The measurement of the deformation field can then be filtered so as to select only that portion associated with the senoidal (sinusoidal) actuation generated by the actuators.

Thus, the signals captured by the optical sensors are filtered in a specific frequency of the senoidal (sinusoidal) signal used in the feeding of the actuators. These filters are used to detect their amplitude and their phase.

Based on the amplitude and phase of the several sensors distributed in a network of sensors attached to the surface of the structural component under monitoring, a two-dimensional map is obtained of the surface strains: amplitudes and phases. By using pattern recognition methods this map is analyzed in order to identify the presence of defects (example: delamination in a composite material or corrosion in a metallic material).

By thus synchronizing actuation with detection it is possible to obtain improved resolution for the strain measurement using fiber Bragg gratings (FBG).

In another aspect, the present example non-limiting embodiment includes a system for monitoring damage to a structural component. The system includes:

a) an actuator operatively connected to the structural component to excite the structural component;

b) a sensor operatively connected to the structural component to measure a vibrational characteristic of the structure in response to excitation of the structure;

c) a tunable laser used as a narrow band light source for the interrogation of the optical fiber sensors;

d) an optical circulator linked with the tunable laser and provided with two outputs: a output transmit the light signal emitted by the tunable laser towards the Bragg grating sensors, and other output, convey the signal reflected by the sensors to a photodetector;

e) a lock-in amplifier;

f) a power amplifier designed to increase the excitation signal provided by the Lock-in (item e);

g) a multiplexer to control the distribution of the excitation harmonic signal (phase and amplitude) by the several piezoelectric actuators;

h) a photo detector to find the light signal reflected by the optical fiber sensors, turning it into an electrical signal conveyed to the lock-in amplifier;

i) an optical fiber multiplexer in order to access the sensors distributed in more than one optical fiber;

j) a computer or other processing element configured to analyze the deformation signals obtaining the deformation field maps and compare them with the reference map, e.g., by performing automatically the detecting, locating and quantification of the damages in the structural component.

BRIEF DESCRIPTION OF THE DRAWINGS

The following detailed description of exemplary non-limiting illustrative embodiments is to be read in conjunction with the drawings of which.

DETAILED DESCRIPTION OF EXAMPLE NON-LIMITING EMBODIMENTS

According to the present example non-limiting embodiment, the expression "structural damage" means delamination, debonding, cracks, peeling, corrosion, wear, crushing, bearing, loss of mass and/or loss of rivet.

The example non-limiting embodiment is directed to a method and a system for the structural health monitoring of composites as well as of metal substrates.

As regards the vibrations designed to induce strains, the system can be operable by vibrations caused from piezoelectric actuators, shape memory alloy, etc., or external vibrations, magnetic fields, acoustic fields, etc.

Example non-limiting embodiments will now be described by relation to the Figures.

Figure 1:
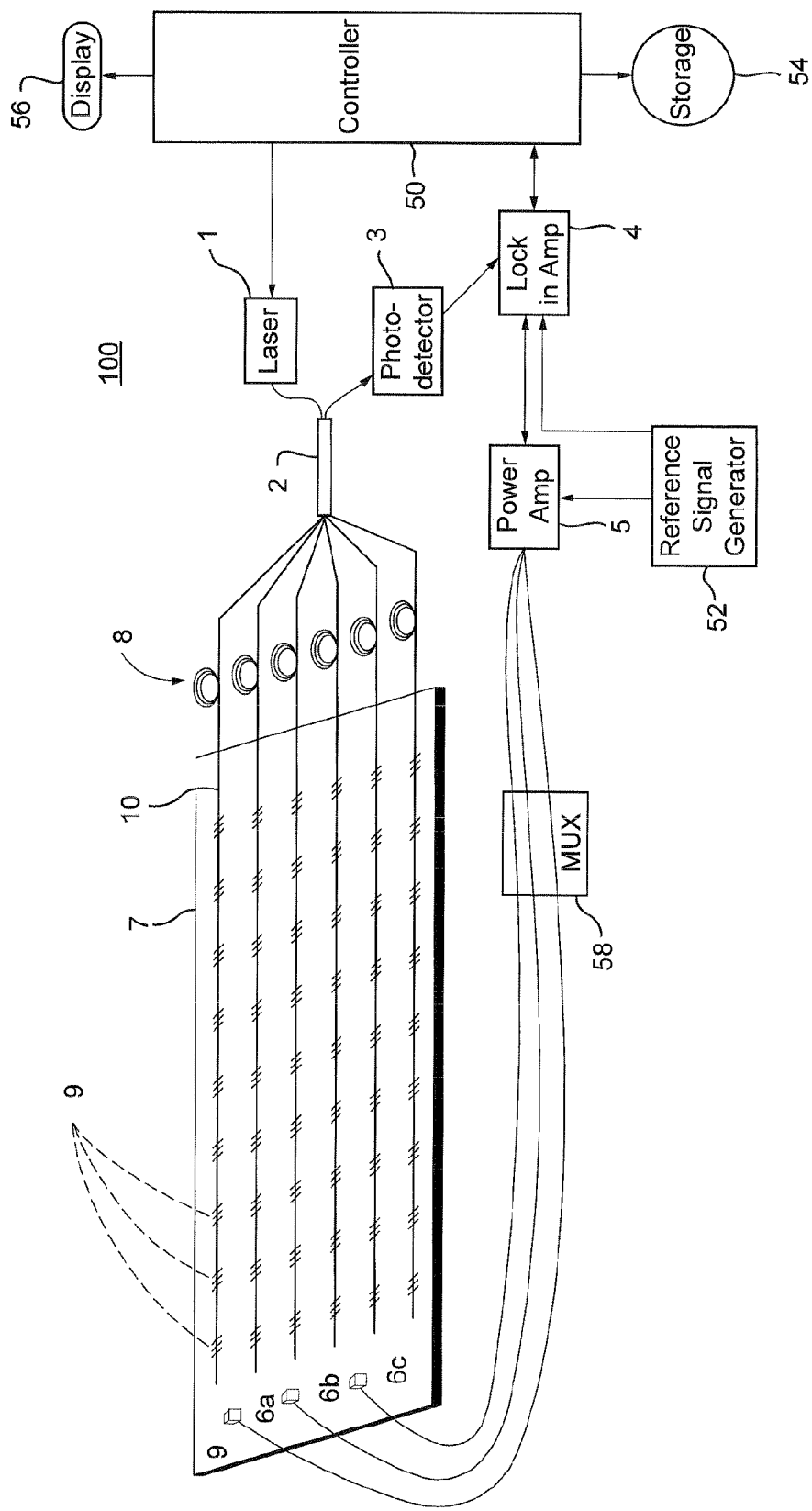
FIG. 1 is an example non-limiting system embodiment of the example non-limiting embodiment for the structural health monitoring (SHM) of an exemplary structural component.

FIG. 1 depicts one non-limiting example non-limiting embodiment of a system (100) designed for the structural health monitoring (SHM) of an exemplary structure. According to FIG. 1, (1) is a tunable laser connected to an optical circulator (2) provided with two outputs: a first output is connected to optical fibers (8) on which are connected a number of fiber Bragg gratings or sensors (9a, 9b, 9c); and a second output is connected to a photo detector (3). The photo detector (3) is in turn linked by any known means to a lock-in amplifier (4). The tunable laser (1) and the lock-in amplifier (4) are connected to a computer or other control processor 50. The lock-in amplifier (4) is also linked to a power amplifier (5) where is connected a number of actuators (6a, 6b, 6c). There can be any number of actuators (6), but for the sake of simplicity only three actuators (6a, 6b, 6c) are represented in this figure.

The actuators (6) are linearly positioned in the boundary of the extremity of structural component (7).

Figure 2:
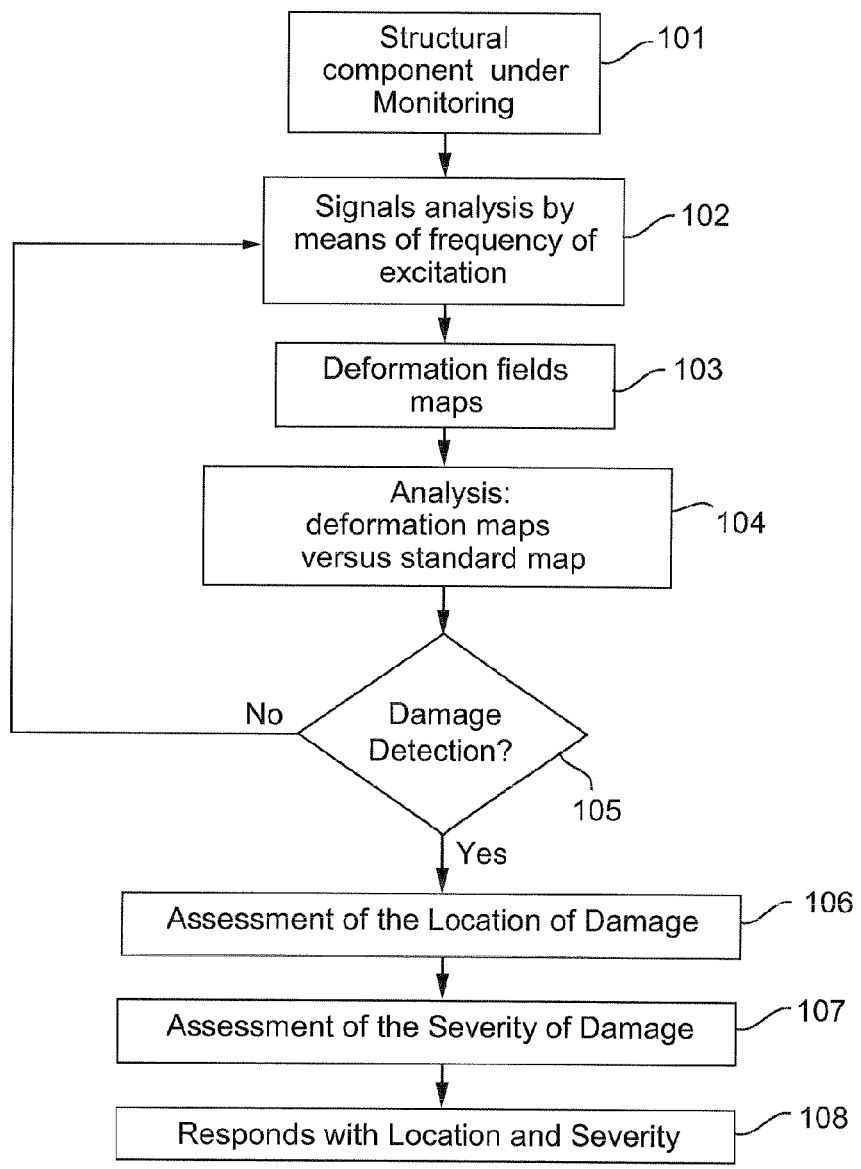
FIG. 2 is a flowchart illustrating an overall method of the example non-limiting embodiment for the structural health monitoring (SHM) of an exemplary structural component.

In the system (100) depicted in FIG. 2, the FBG sensors (9) sense the amplitude and the phase of vibrational characteristics of structural component 7. These sensed amplitudes and phases encoded in laser light are selected by optical circulator 2, one light signal at a time, to photodetector 3. Photodetector 3 converts the received light signal to an analog electrical signal and provides the analog electrical signal to lock-In amplifier (4). Lock-in amplifier (4) comprises a conventional analog dual phase lock-in amplifier that measures the amplitude and phase of signals using a synchronous detection process to recover the signals. Lock-in amplifier (4) acts as a narrow-bandpass filter that removes unwanted noise while allowing through the signal that is to be measured. The frequency of the signal to be measured and thus the passband region of the filter is set by a reference signal, which is supplied by reference signal generator 52 to the lock-in amplifier along with the signal detected by the photodetector 3. The reference signal the reference signal generator 52 generates is at the same frequency as the modulation of the photodetector signal to be measured since the reference signal is also supplied to actuators 6. The lock-in amplifier (4) thus compares the frequency of the signal measured by photodetector (3) with the reference signals generated for the actuators (6). In this way the signals obtained by sensors (9) and the signals generated by the actuators (6) are synchronized. For each frequency of excitation, all the information generated by sensors (9) is stored in storage device 54 so as to be analyzed in order to evaluate the integrity of the structural component (7).

The example non-limiting embodiment of system 100 comprises a set of at least two Bragg gratings 9 written along at least one optical fiber 10. The Bragg gratings 9 are attached (mechanically coupled) to the surface of the structural component 7 or embedded within the structural component, in the region where are defined to effect the monitoring, and provide strain measurements.

A set of piezoelectric actuators 6 made up of at least one actuator are attached (mechanically coupled) to the surface of the structural component or embedded in its structure.

A tunable laser 1 is used as a narrow band light source for the interrogation of the optical fiber sensors 9. The laser light source 1 sweeps a wide band of wave lengths so as to interrogate all the Bragg grating sensors 9 installed in the structural component 7 under monitoring. Different FBGs 9 can be written to reflect different light frequencies such that sweeping the laser light source across a band of light frequencies allows the system 100 to acquire strain characteristics sensed by disparately-located FBGs 9. The capability of an FBG 9 to measure strain is well known in the art.

Optical circulator 2 is provided with two outputs: a first output sends the light signal emitted by the tunable laser 1 towards the Bragg grating sensors 9, and another output sends the signal reflected by the sensors back along the same optical fibers 10 to a photo detector 3.

Lock-in amplifier 4 has a double function: (i) to use its own reference signal (from reference signal generator 52) to provide a harmonic signal for excitations of the piezoelectric actuators 6; and (ii) to recover the amplitude and phase of the senoidal (sinusoidal) strain signals, at this same frequency component, produced exclusively by the piezoelectric actuators 6 harmonically excited.

Power amplifier 5 is designed to increase the excitation signal provided by the Lock-in amplifier reference signal generator 52. In the proposed non-limiting system, the piezoelectric actuators are fed by a continuous wave (CW) signal.

A multiplexer 58 is used to control the distribution of the excitation harmonic signal (phase and amplitude) by the several piezoelectric actuators 6.

Photo detector 3 is used to find the light signal reflected by the optical fiber sensors 9, turning it into an electrical signal conveyed to the lock-in amplifier 4.

An optical fiber multiplexer 2 can be used in order to access more than one optical fiber in the case the sensors are distributed on more than one optical fiber 10.

According with the example non-limiting embodiment the system for the structural health monitoring (SHM) of a structural component, a computer or other processing element 50 designed to (i) control the inspections by means of software, hardware, firmware or a combination thereof; and (ii) analyze the deformation signals so as to obtain the deformation field maps and compare them with the reference map, with detecting, locating and quantification of the damages in the structural component or the monitoring of the growth of some previously detected damage. That is, artificial intelligence-based software for pattern recognition performs automatically the comparison between deformation field's maps.

FIG. 2 is a simplified flow-chart of a method according to the example non-limiting embodiment, which may be executed by processor 50 under control of software code stored in storage 54. According to this flowchart, (101) means the structural component is under monitoring. Then at (102) signal analysis is performed by means of frequency of excitation as described above. A deformation field map is generated at (103). The comparison between deformation field map generated with a deformation field map of reference or baseline is performed at (104). The damage detection (difference between the two maps) is evaluated by (105). In the absence of damage, the method returns to (101) and repeats steps (101) to (104). If any damage is detected, the method performs operations leading to the assessment of the Location of Damage at (106), followed by the assessment of the Severity of Damage at (107) and response with location and severity of damage at (108).

An example non-limiting method for the structural health monitoring (SHM) of a structural component having at least an actuator and at least a sensor or a group of actuator and group of sensors may thus comprise:

a) Excitation in-phase or out-of-phase with a pre-determined frequency range to excite the said structural component 7, so as to generate a dynamic deformation field, with senoidal (sinusoidal) timed variation at the same frequency of the potential difference imposed on the piezoelectric elements 6;

b) filtering the measurement of the deformation field to select only the range of the deformation field associated with the senoidal (sinusoidal) actuation generated by the actuators 6;

c) obtaining a two-dimensional map with the amplitudes and phases of the surface strains, where these maps are based in the amplitude and in the phase of the several sensors 9 distributed in a network of sensors 9 attached to the surface of the structural component under monitoring;

d) repeating the procedure for multiple frequencies range;

e) comparing the two-dimensional maps obtained by the different frequencies in the analysis for detection of structural damage; and f) computational analysis of the so-obtained two-dimensional field deformation maps with the aid of pattern recognition methods in order to identify structural damage.

Figure 3:
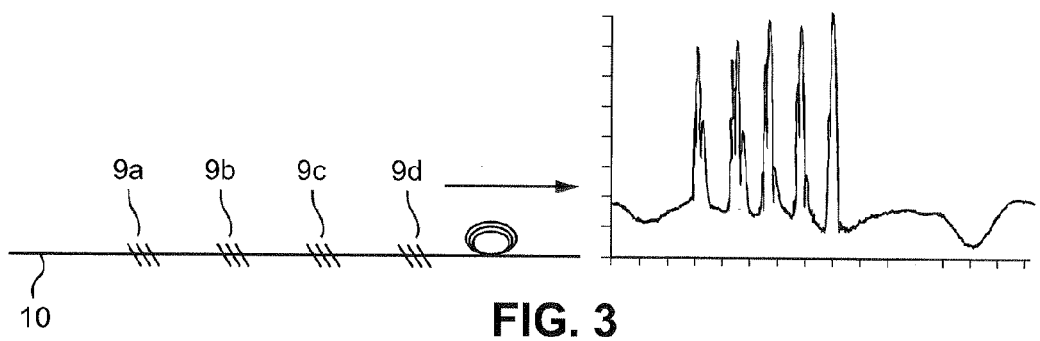
FIG. 3 is an example plot which represents the reflection spectrum of five FBG sensors, when irradiated with a wide band optical source.

FIG. 3 is a plot which represents the reflection spectrum of five FBG sensors, when irradiated with a wide band optical source. In the example embodiment, the photodetector 3 converts the reflection spectrum to an electrical signal that can be analyzed in the frequency domain. While it would be possible for controller 50 to provide a digital signal processor using FFT technology, the preferred non-limiting embodiment uses a simpler technique of a synchronous lock-in amplifier to synchronously detect the frequency and phase of the detected electrical signal.

Figure 4:
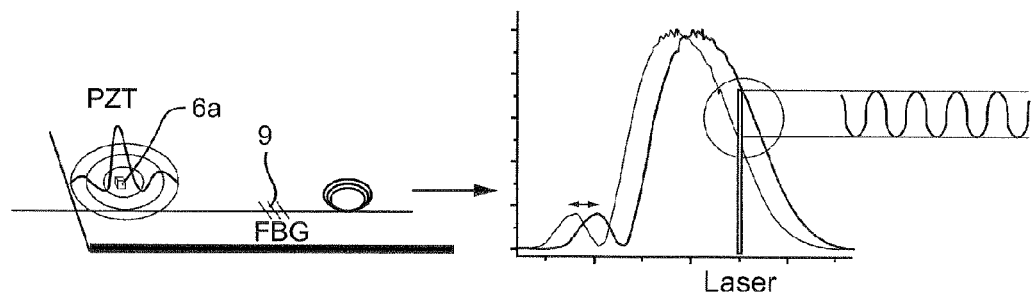
FIG. 4 shows the shift of the reflection spectrum of a FBG sensor and the variation of the amplitude in the inferred signal, when a mechanical excitation on the structure of interest is caused by a PZT actuator.

FIG. 4 shows the example shift of the reflection spectrum of an example FBG sensor and variation of the amplitude in the inferred signal, when a mechanical excitation on the structure of interest is caused by a PZT actuator 6a. If the PZT actuator excitation is sinusoidal, the resulting FBG-detected signal will show a phase shift that changes sinusoidally. This phase shift can be synchronously detected by lock-in amplifier (4). These signals can be stored in storage 54 along with other signals stored for other frequencies and other sensors 6. The processor 50 executes a stored program to analyze the stored signals and generate a graphical deformation map for display on graphical display 56.

Figure 5A:
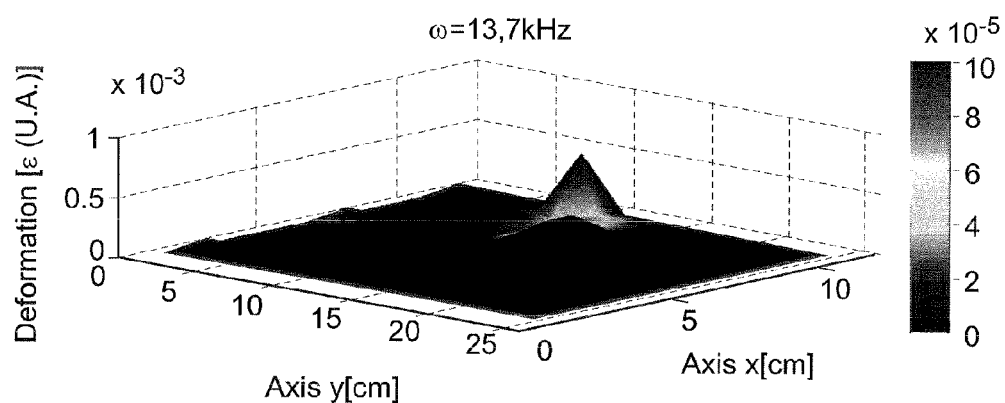
FIGS. 5a & 5b illustrate example three-dimensional and two-dimensional field deformation maps.

FIG. 5a illustrates an example 3D deformation map. The 3D map indicates a square delamination is at the center of the plate. As can be seen, the deformation map plots deformation (εU.A.) against position (x, y). In this case, the deformation is represented by strain ε—which is defined as the amount of deformation per unit length of an object when a load is applied. Strain ε is calculated by dividing the total deformation of the original length by the original length (L): $\varepsilon=\Delta L/L$. Typical values for strain are less than 0.005 inch/inch and are often expressed in micro-strain units (i.e., $10^{-6}$). Note the scale on the right-hand side of FIG. 5a showing Strain ε in units of $0\text{-}10\times10^{-6}$. In the example embodiment, the amount of Strain ε can be encoded in a visible color spectrum with for example higher strains of $\varepsilon=10\times10^{-5}$ showing red and lower strains of $\varepsilon=0$ showing violet, and strains in between distributed along the "ROYGBIV" colors of the rainbow. The FIG. 5a deformation map further graphically shows the topography of strain, with lower strains having lower elevation and higher strains having higher elevations or peaks. Through such visualization, it is possible to see which parts of the structural element are under how much strain. The FIG. 5b deformation map visualization is 2D and uses color encoding as described above to allow visualization of the amount of strain. Other representations are possible.

The example non-limiting embodiment will now be illustrated by the Example shown the follows.

Example

By means of numerical simulations were obtained the deformation maps related to the behavior of a composite plate. The composite plate has 16 superimposed layers, which were submitted to mechanical vibration caused by PZT actuators 6.

Several delamination models were tested by varying dimensions (length and width). For each tested model, 40 excitation frequencies varying from 11.1 kHz to 15.0 kHz with a 0.1 kHz step were simulated. In this way, for each delamination model, 40 deformation maps were obtained.

For this test, the frequency of excitation was $\omega=13.7$ kHz. The deformation map 5a shows a square delamination is at the center of the plate (coordinate x=0.250 m and coordinate y=0.125 m), between layers 4 and 5.

Figure 5B:
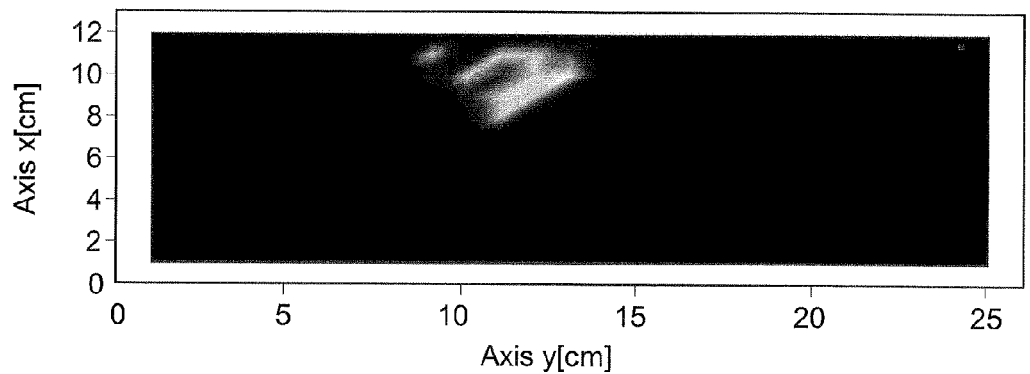

From FIG. 5a, 5b it is clear that a deformation pattern of the order of 10 microstrain is present on the delamination region.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

The invention claimed is:

1. A method for monitoring the structural health (SHM) of a structural component of a type that has plural fiber Bragg grating (FBG) sensors distributed in a network of FBG sensors attached to a surface of the structural component, the method comprising:
   a) with at least one actuator, exciting the structural component using CW (continuous waves) across a predetermined frequency range to generate a dynamic deformation field thereby imposing sinusoidally defined variation at the same frequency of a potential difference on plural fiber Bragg grating (FBG) sensors distributed in the network of FBG sensors attached to the surface of the structural component;
   b) sensing a deformation field using the plural fiber Bragg grating (FBG) sensors distributed in the network of FBG sensors attached to the surface of the structural component, including synchronizing actuation of said at least one actuator with sensing using the plural fiber Bragg grating sensors to obtain in-phase and out-of-phase measurement resolution for strain measurements using the plural fiber Bragg gratings;
   c) filtering the sensed deformation field to select only that portion of the sensed deformation field associated with the sinusoidal actuation generated by the at least one actuator;
   d) in response at least in part to the filtered sensed deformation field, generating a two-dimensional deformation field map indicating the amplitudes and phases of surface strains, said deformation field map being based on the amplitude and phase sensed by the plural sensors;
   e) repeating steps (a)-(d) for multiple excitation frequencies of the at least one actuator to provide additional corresponding two-dimensional deformation field map(s);
   f) comparing the two-dimensional deformation field maps obtained by the different excitation frequencies to detect structural damage; and
   g) performing computational analysis of the two-dimensional field deformation field maps with the aid of pattern recognition to identify structural damage.

2. The method according to claim 1, wherein the frequency of actuation is different based on frequency ranges associated with primary and secondary loads as well as based on temperature variations in the said structural component.

3. The method according to claim 1, wherein said filtering excludes not only the amplitude but also phase, and selects only a specific frequency of a sinusoidal signal used in the feeding of the at least one actuator.

4. The method according to claim 1, wherein the method further includes obtaining a baseline two-dimensional deformation field map for comparison when the structural component under monitoring is free from defects or bears known defects.

5. The method according to claim 1, wherein the method is substantially unaffected by changes in structural component temperature.

6. A system for the structural health monitoring (SHM) of a structural component, comprising:
   a computer configured to (i) control inspections by executing software; and (ii) analyze deformation signals to obtain deformation field maps and compare the deformation field maps with a reference map, for detecting, locating and quantifying damage in the structural component or monitoring growth of some previously detected damage;
   a set of at least two Bragg gratings written along at least one optical fiber, the Bragg gratings forming sensors, the sensors being longitudinally positioned on the said structural component under monitoring, the Bragg gratings being attached to a surface of the structural component and configured to effect monitoring, and to provide strain measurements;
   a set of piezoelectric actuators comprising at least one actuator, attached to the surface of the structural component or embedded in the structure of the structural component and fed by a CW signal;
   a tunable laser used as a narrow band light source for interrogating the optical fiber sensors, the laser being configured to sweep a wide band of wavelengths to interrogate the Bragg grating sensors installed in the component under monitoring;

an optical circulator providing at least first and second outputs, the first output sending a light signal emitted by the tunable laser towards the Bragg grating sensors, the second output sending the signal reflected by the sensors to a photo detector;

a lock-in amplifier configured to perform a double function: (i) to use its own reference signal to provide a harmonic signal for excitations of the set of piezoelectric actuators; and (ii) to recover the amplitude and phase of the sinusoidal strain signals, at the same frequency component, produced by the harmonically excited piezoelectric actuators;

a power amplifier configured to increase the excitation signal provided by the lock-in amplifier;

a multiplexer configured to control the distribution of the excitation harmonic signal (phase and amplitude) by the piezoelectric actuators;

the photo detector configured to detect the light signal reflected by the optical fiber sensors, turning the detected light signal into an electrical signal and conveying the signal to the lock-in amplifier; and an optical fiber multiplexer structured to access more than one optical fiber in the case the sensors are distributed on more than one optical fiber.

7. A system for monitoring the structural health (SHM) of a structural component of a type that has plural fiber Bragg grating (FBG) sensors distributed in a network of FBG sensors attached to a surface of the structural component, the system comprising:

at least one actuator coupled to the structural component, the actuator exciting the structural component using CW (continuous waves) across a predetermined frequency range to generate a dynamic deformation field thereby imposing sinusoidally defined variation at the same frequency of a potential difference on the plural fiber Bragg grating (FBG) sensors distributed in the network of FBG sensors attached to the surface of the structural component;

a detector that is coupled to the plural fiber Bragg grating sensors, the detector being configured to detect a deformation field using the plural fiber Bragg grating sensors in a manner that synchronizes detection by said plural fiber Bragg grating sensors with actuation of said at least one actuator to obtain in-phase and out-of-phase measurement resolution for strain measurements using the plural fiber Bragg gratings;

a filter configured to filter the detected deformation field to select only that portion of the detected deformation field associated with the sinusoidal actuation generated by the at least one actuator;

a map generator configured to generate, in response at least in part to the filtered detected deformation field, a two-dimensional deformation field map indicating the amplitudes and phases of surface strains, said two-dimensional deformation field map being based on the amplitude and phase sensed by the plural sensors;

the at least one actuator, the detector, the filter and the map generator cooperating to use multiple frequencies to provide additional corresponding two-dimensional deformation field map(s); and at least one processor comparing the two-dimensional deformation field maps obtained by the different excitation frequencies to detect structural damage;

the at least one processor operatively coupled to the comparator and the map generator, the at least one processor performing computational analysis of the two-dimensional field deformation maps with the aid of pattern recognition in order to identify structural damage.

8. The system according to claim 7, wherein the frequency of actuation is different based on frequency ranges associated with primary and secondary loads as well as based on temperature variations in the said structural component.

9. The system according to claim 7, wherein said filter is configured to exclude not only the amplitude but also phase, and to select only a specific frequency of a sinusoidal signal used in feeding of the at least one actuator.

10. The system according to claim 7, wherein the map generator is further configured to obtain a baseline two-dimensional deformation field map for comparison when the structural component under monitoring is free from defects or bears known defects.

11. The system according to claim 7, wherein the system is substantially unaffected by changes in structural component temperature.

12. A method for the structural health monitoring (SHM) of a structural component, comprising:

using at least one computer: (i) controlling inspections by executing software; and (ii) analyzing deformation signals to obtain deformation field maps and compare the deformation field maps with a reference map, for detecting, locating and quantifying damage in the structural component or monitoring growth of some previously detected damage;

effecting monitoring and providing strain measurements using a set of at least two Bragg gratings written along at least one optical fiber, the Bragg gratings forming sensors, the sensors being longitudinally positioned on the said structural component under monitoring, the Bragg gratings attached to a surface of the structural component;

feeding a CW signal to a set of piezoelectric actuators comprising at least one actuator, attached to the surface of the structural component or embedded in the structure of the structural component;

interrogating the optical fiber sensors using a tunable laser as a narrow band light source, including sweeping the laser across a wide band of wavelengths to interrogate all the at least two Bragg grating sensors installed in the component under monitoring;

sending, from a first output of an optical circulator providing at least first and second outputs, a light signal emitted by the tunable laser towards the Bragg grating sensors, sending, from a second output of the optical circulator, a signal reflected by the sensors to a photo detector;

using a lock-in amplifier to perform a double function of: (i) using its own reference signal to provide a harmonic signal for excitations of the piezoelectric actuators; and (ii) recovering the amplitude and phase of the sinusoidal strain signals, at the same frequency component, produced by the harmonically excited piezoelectric actuators;

using a power amplifier to increase the excitation signal provided by the lock-in amplifier;

controlling the distribution of the excitation harmonic signal (phase and amplitude) by the piezoelectric actuators with a multiplexer;

using the photo detector to detect the light signal reflected by the optical fiber sensors, turn the detected light signal into an electrical signal, and convey the signal to the lock-in amplifier; and using an optical fiber multiplexer to access more than one optical fiber in the case the sensors are distributed on more than one optical fiber.

* * * * *